United States Patent
Davila et al.

(10) Patent No.: US 10,799,313 B2
(45) Date of Patent: Oct. 13, 2020

(54) TISSUE EXPANDER WITH PECTORAL ATTACHMENT

(71) Applicant: MENTOR WORLDWIDE LLC, Santa Barbara, CA (US)

(72) Inventors: Luis Alberto Davila, Alpharetta, GA (US); Udo Werner Graf, Goleta, CA (US); John Wesley Canady, Iowa City, IA (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 449 days.

(21) Appl. No.: 14/656,327

(22) Filed: Mar. 12, 2015

(65) Prior Publication Data
US 2016/0262835 A1    Sep. 15, 2016

(51) Int. Cl.
*A61F 2/12* (2006.01)
*A61B 90/00* (2016.01)

(52) U.S. Cl.
CPC ............... *A61B 90/02* (2016.02); *A61F 2/12* (2013.01); *A61F 2220/0008* (2013.01); *A61F 2250/0003* (2013.01); *A61F 2250/0059* (2013.01)

(58) Field of Classification Search
CPC ..... A61F 2/12; A61F 2250/0003; A61B 90/02
See application file for complete search history.

(56) References Cited

U.S. PATENT DOCUMENTS

| | | | |
|---|---|---|---|
| 3,858,248 A | 1/1975 | Crowe | |
| 4,125,117 A | 11/1978 | Lee | |
| 4,902,294 A | 2/1990 | Gosserez | |
| 4,950,292 A * | 8/1990 | Audretsch | A61F 2/12 623/8 |
| 2003/0149481 A1 | 8/2003 | Guest et al. | |
| 2012/0221105 A1 | 8/2012 | Altman et al. | |
| 2013/0253646 A1 | 9/2013 | Altman et al. | |
| 2013/0325120 A1 | 12/2013 | McClellan | |
| 2015/0012089 A1 * | 1/2015 | Shetty | A61F 2/0059 623/8 |

(Continued)

FOREIGN PATENT DOCUMENTS

| | | |
|---|---|---|
| CN | 101658444 A | 3/2010 |
| EP | 0338701 A2 | 10/1989 |
| JP | 2011502719 A | 1/2011 |

OTHER PUBLICATIONS

PCT/US2016/017509—International Search Report dated Jun. 6, 2016.

(Continued)

*Primary Examiner* — Diane D Yabut
(74) *Attorney, Agent, or Firm* — Eugene L. Szczecina, Jr.

(57) ABSTRACT

A mammary tissue expander device including an inflatable shell having an anterior side and a posterior side, the anterior side having an upper pole portion and a lower pole portion meeting at an apex, and an injection port for receiving fluid therethrough to inflate the expander, and a substantially flat attachment flap coupled to the posterior side of the shell, and extending in an inferior direction beyond an inferior edge of the shell by a distance D such that the attachment flap may be extended around the inferior edge and upwards to overlay at least a portion of the anterior side of the shell.

11 Claims, 3 Drawing Sheets

(56) References Cited

U.S. PATENT DOCUMENTS

2015/0025563 A1* 1/2015 Mosharrafa ............ A61B 19/24
606/191

OTHER PUBLICATIONS

CN Application No. 201680016006.5—Chinese Search Report dated Sep. 23, 2019.
JP Application No. 2017-566606—Japanese Office Action Translation dated Jan. 7, 2020.
AU Application No. 2016229479—Australian Full Examination Report dated Jan. 13, 2020.

* cited by examiner

TISSUE EXPANDER WITH PECTORAL ATTACHMENT

FIELD OF THE INVENTION

The present invention relates generally to the field of implantable tissue expanders, and more particularly to implantable mammary soft tissue expanders having an attachment device for securing the pectoral muscle during expansion.

BACKGROUND

Tissue expanders are devices that are implanted beneath the skin and then gradually inflated to stretch the overlying tissue. Such expanders are used to create a pocket for receiving a permanent prosthesis and/or to generate increased skin surface area so that skin can be utilized for grafting or reconstruction.

In the case of mammary implants, tissue expanders are used to create the mammary pocket that will ultimately receive the permanent mammary implant. These expanders are commonly formed of a silicone polymer shell and are implanted in a collapsed state. After implantation, saline or some other fluid is periodically injected into the expander over time, for example through an injection port, until the desired sized pocket is achieved.

Breast reconstruction following a mastectomy is usually performed in two stages. The tissue expander is used in the first stage and is placed under a section of the pectoralis major muscle. For this to occur, the lower edge of the pectoralis major muscle must be released along its inferior edge and re-attached with the use of a surgical mesh or Acellular Dermal Matrix (ADM). If this mesh or ADM detaches early in the expansion process, it can result in the muscle retracting or recoiling over the top of the tissue expander; an occurrence that is sometimes referred to as "window shading." This is undesirable in that it can result in visible defects in the lower pole in those areas that have skin only coverage as opposed to coverage from the combination of skin and muscle. Window shading can also cause patient discomfort and an inadequate expansion process. This would result in a surgical re-intervention to re-attach the inferior edge of the pectoralis muscle.

Thus, it would be desirable to provide an expander that eliminates or greatly reduces the need for a mesh or ADM, while providing a means to prevent window shading.

SUMMARY OF THE INVENTION

A mammary tissue expander is provided including an inflatable shell having an anterior side and a posterior side, with the anterior side having an upper pole portion and a lower pole portion meeting at an apex, and an injection port for receiving fluid therethrough to inflate the expander. The expander further includes a substantially flat attachment flap coupled to the posterior side of the shell and extending in an inferior direction beyond an inferior edge of the shell by a distance D such that the attachment flap may be extended around the inferior edge and upwards to overlay at least a portion of the anterior side of the shell.

The expander may be extended upwards to overlay the lower pole and apex of the shell, and may have a distance D that is greater than or equal to 8 cm.

According to one embodiment, when the attachment flap is extended around the inferior edge of the shell and upwards, the outer perimeter of the attachment flap lies substantially within an outer perimeter of the shell.

The shell of the expander may be comprised of silicone, and the attachment flap may be comprised of a mesh material, such as a polypropylene mesh.

According to one alternate embodiment, the mesh material is encapsulated on both sides with silicone.

In yet another embodiment, the expander further includes at least one fixation tab coupled to the posterior side of the shell and extending outwardly from the shell, and may further include at least one aperture corresponding to each fixation tab. In yet another embodiment, the at least one aperture is positioned so that the corresponding fixation tab may pass freely therethrough when the attachment flap is extended around the inferior edge and upward across at least a portion of the anterior side of the shell. The at least one aperture may further have a size and shape substantially similar to a size and shape of the corresponding fixation tab.

In yet another embodiment, the attachment flap further includes a plurality of holes therein.

A method is also provided for tissue expansion that includes the steps of providing a mammary tissue expander having an inflatable shell having an anterior side and a posterior side, the anterior side having an upper pole portion and a lower pole portion meeting at an apex, and an injection port for receiving fluid therethrough to inflate the expander, and a substantially flat attachment flap coupled to the posterior side of the shell, and extending in an inferior direction beyond the lower pole of the shell; implanting the tissue expander in a female patient such that the posterior side is positioned against the patient's chest wall and the lower pole portion is positioned inferior to the upper pole portion, and such that the expander is placed under a section of the patient's pectoralis muscle; and wrapping the attachment flap from the posterior side around an inferior edge of the shell and upward across at least a portion of the anterior side of the shell.

The shell may further include at least one fixation tab coupled to the posterior side of the shell and extending outwardly from the shell, and the attachment flap may further include at least one aperture therein corresponding to the at least one fixation tab. During the wrapping step, the at least one fixation tab passes freely through the at least one corresponding aperture.

In one embodiment, the shell is made of silicone and the attachment flap is made of a mesh material. In yet another embodiment, the mesh material of the attachment flap is encapsulated with silicone on both sides.

Also provided is a tissue expander having an inflatable shell having an anterior side and a posterior side with the anterior side having an injection port for receiving fluid therethrough, and a substantially flat attachment flap coupled to the posterior side of the shell and extending in an inferior direction beyond an inferior edge of the shell by a distance of at least 8 cm.

These and other objects, features and advantages of the present invention will be apparent from the following detailed description of illustrative embodiments thereof, which is to be read in connection with the accompanying drawings.

DETAILED DESCRIPTION

Figure 1B:
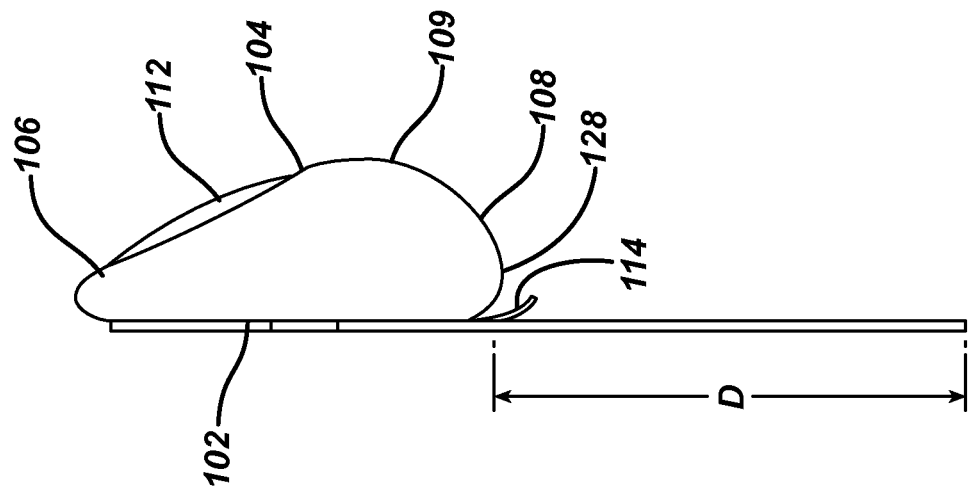
FIGS. 1a and 1b are front and side views of an expander according to the present disclosure.
Figure 1A:
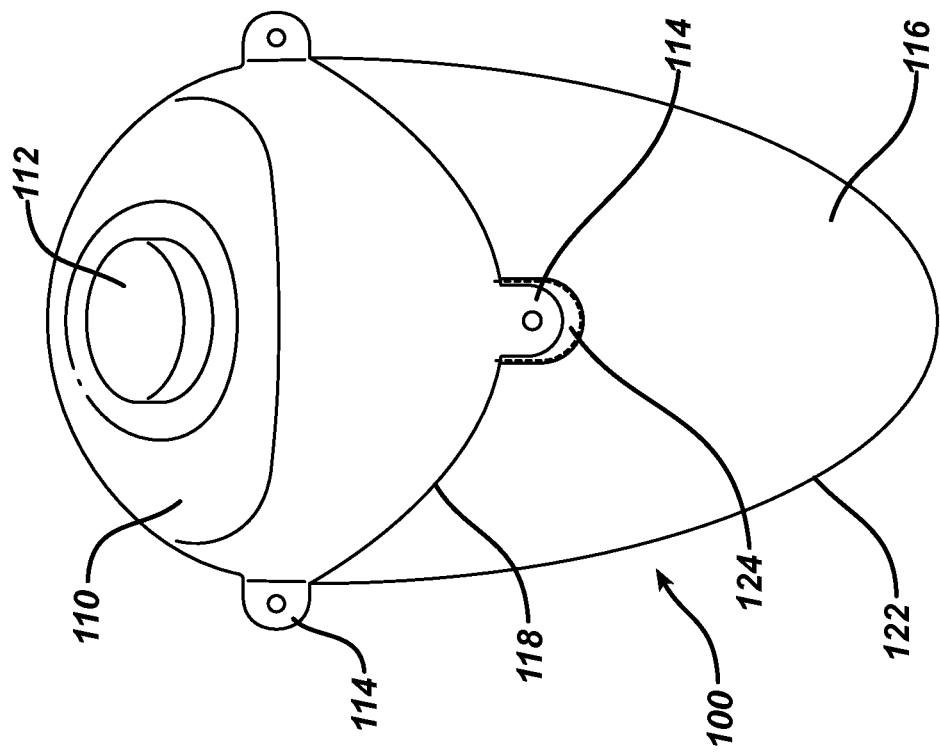

FIGS. 1a and 1b show front and side views of an exemplary expander 100 according to the present disclosure. The expander has a posterior side 102 that lies substantially flat against the patient's chest wall and an anterior side 104 that faces outward from the chest wall when implanted. The anterior side 104 includes an upper pole region 106 (i.e., the upper portion of the shell when the implant recipient is standing), a lower pole region 108 (i.e., the lower portion of the shell when the implant recipient is standing) and an apex 109 (corresponding to the point at which the nipple would be in a natural breast) separating the upper pole region and the lower pole region. The outer shell 110 of the expander 100 is typically made of a silicone material and includes an injection port or other valve 112 through which saline or another fluid is injected over time into the contained space defined by the outer shell 110. The expander shell 110 can have a smooth or textured surface.

Figure 2:
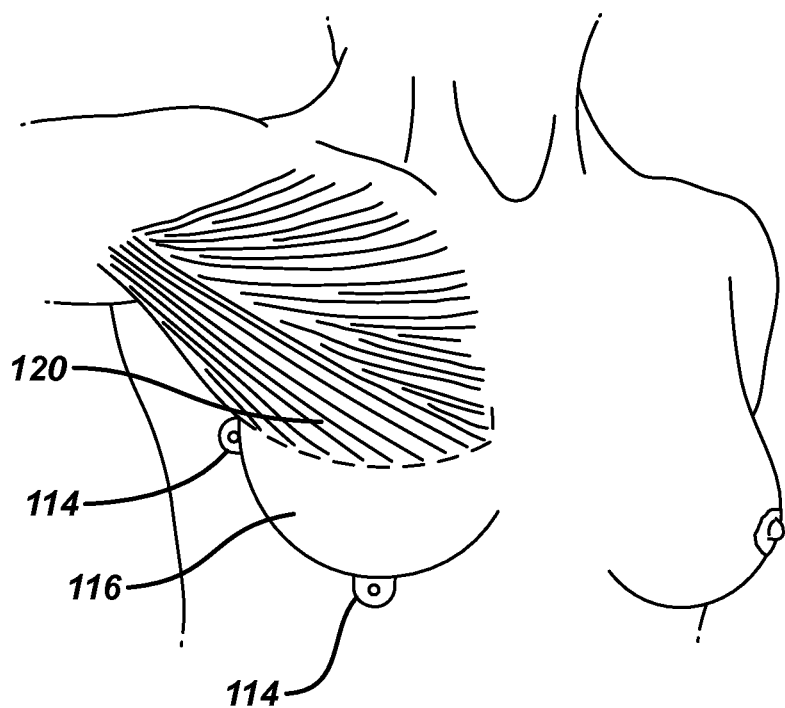
FIG. 2 is a perspective view illustrating positioning of the expander of FIG. 1 within a patient.
Figure 3:
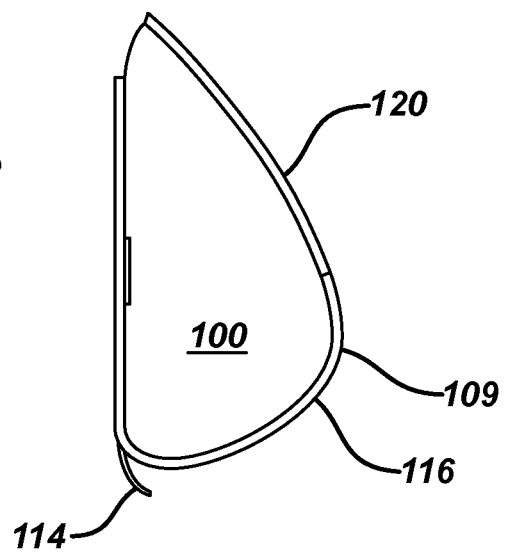
FIG. 3 is a side view illustrating positioning of the expander of FIG. 1 relative to a patient's pectoral muscle.

The expander 100 may include one or more fixation tabs 114 coupled to and extending preferably from the posterior side 102. The fixation tabs 114 are used to aid the surgeon in securing the expander to the chest wall to maintain its position during expansion, typically by using sutures or the like. In this regard, the fixation tabs further safeguard against accidental puncture of the implant shell. The expander of the present disclosure further includes a substantially flat, flexible attachment flap 116 that extends from the posterior side of the implant in an inferior direction (toward a patient's feet) beyond the outer perimeter 118 of the expander. This flap can also be smooth or textured similar to the outer shell 110. Referring now to FIG. 3 in conjunction with FIG. 1, the attachment flap 116 extends beyond the perimeter of the expander by a distance D such that, when the expander is implanted, the attachment flap can be extended or wrapped around the inferior edge 128 of the implant, and up across at least a portion of the lower pole of the expander and to the anterior side of the implant, and in a preferred embodiment past the apex 109 to a point where it can be attached to the previously released pectoral muscle 120 by suturing or any other suitable means, as is further illustrated in FIG. 2. In a preferred embodiment distance D is approximately 8-18 cm, and more preferably 12 cm. The attachment flap is coupled to the posterior side of the implant b any suitable means, such as silicone bonding (un-vulcanized to vulcanized material bonding). In the illustrated embodiment, the attachment flap substantially covers the entire posterior side of the implant. This is not required; however, as it is significant only that it extends beyond the inferior edge of the shell as described above.

The overall shape of the attachment flap is designed to closely follow that of the expander when in use. The attachment flap has an outer perimeter 122 that defines its overall shape and is designed so that when wrapped around the anterior side of the implant as described above, the outer perimeter 122 of the attachment flap closely follows the outer perimeter of the expander as is best illustrated in FIG. 2. Preferably, the outer perimeter of the attachment flap will lie slightly within the outer perimeter of the shell. The end of the attachment flap may be trimmed, however, so that it aligns with the end of the pectoral muscle.

Figure 5:
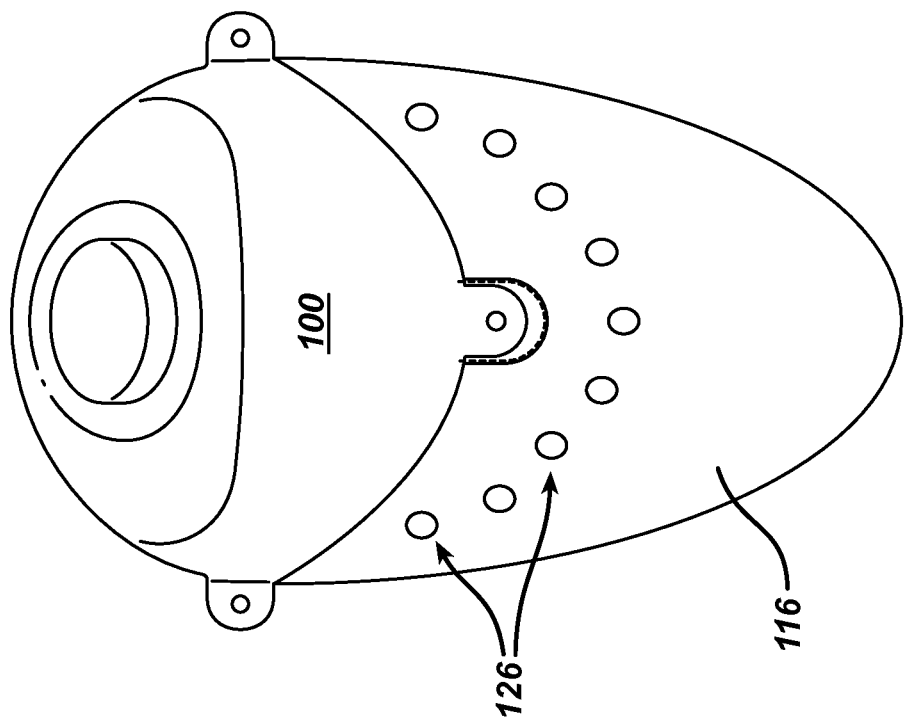

Referring once again to FIG. 1, if the expander device includes fixation tabs 114 as shown, then the attachment flap 116 further includes corresponding apertures 124 therein. The apertures 124 preferably have a shape that substantially corresponds to that of the fixation tab as shown, and is positioned on the attachment flap so that when the attachment flap is wrapped around the anterior side of the implant, the attachment flap can freely pass over the fixation tabs without any obstruction. In this regard, the apertures need not correspond directly in shape to the fixation tabs, but must at least be of an adequate size, shape and position so that the fixation tabs may pass freely through the aperture when the attachment flap is wrapped around the anterior side of the implant. FIG. 5 illustrates an alternative embodiment of an expander device having a different shape fixation tab and attachment flap aperture. As is readily apparent to those skilled in the art, any suitable configuration of these components is within the scope of the present disclosure.

Figure 4:
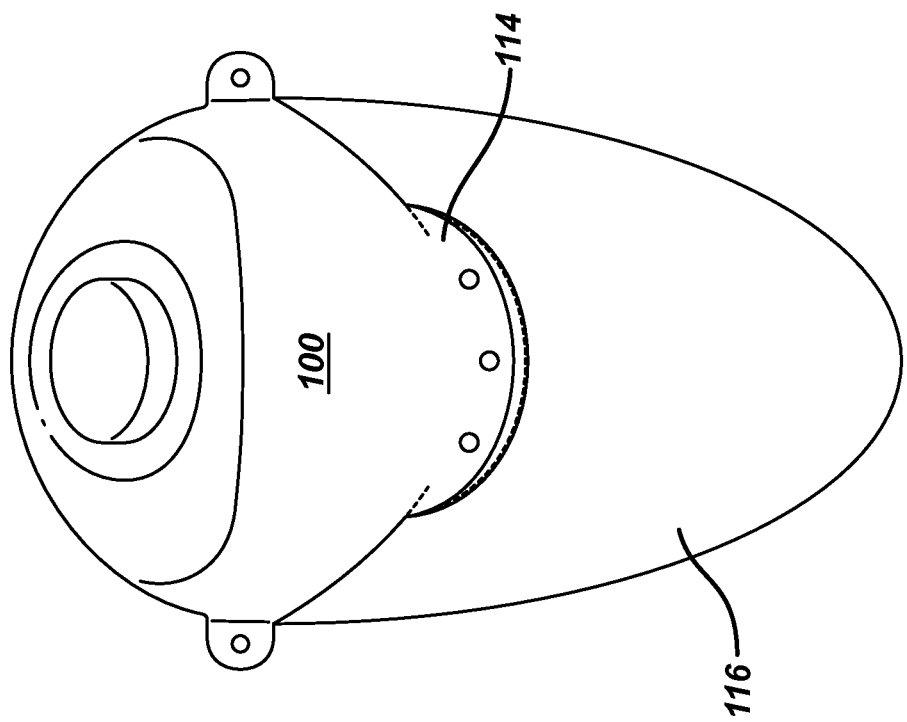
FIGS. 4 and 5 front views of alternative embodiments of the expander of FIG. 1.

FIG. 4 illustrates an alternative embodiment where the attachment flap further includes a plurality of additional apertures 126. The apertures could have multiple sizes/shapes and would allow for fluid to flow.

Any known expander can be used in accordance with the present disclosure. For example, the CPX4 Contour Profile Tissue Expander with Tabs, which is manufactured and sold by Mentor Worldwide LLC of Santa Barbara, Calif., is particularly suitable. The attachment flap can be made of any suitable, implantable reinforcement material, such as Vicryl™ (polyglactin 910) or Dacron® (polyethylene terephthalate). The mesh could be encapsulated in silicone. In a preferred embodiment, the attachment flap is a Dacron® mesh that is encapsulated by silicone material on both sides.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A mammary tissue expander device comprising:
    an inflatable shell having an anterior side and a posterior side, the anterior side having an upper pole portion and a lower pole portion meeting at an apex, and an injection port for receiving fluid therethrough to inflate the expander; and
    a substantially flat attachment flap coupled to the posterior side of the shell, and extending in an inferior direction beyond an inferior edge of the shell by a distance D such that the attachment flap may be extended around the inferior edge and upwards to overlay substantially curved on at least a portion of the anterior side of the shell.

2. The expander according to claim 1, wherein the attachment flap may be extended upwards to overlay the lower pole and apex of the shell.

3. The expander according to claim 1, wherein when the attachment flap is extended around the inferior edge of the shell and upwards, the outer perimeter of the attachment flap lies substantially within an outer perimeter of the shell.

4. The expander according to claim 1, wherein the shell is comprised of silicone, and wherein the attachment flap is comprised of a mesh material.

5. The expander according to claim 4, wherein the mesh material is a polypropylene mesh.

6. The expander according to claim 4, wherein the mesh material is encapsulated on both sides with silicone.

7. The expander according to claim 1, further comprising at least one fixation tab coupled to the posterior side of the shell and extending outwardly from the shell.

8. The expander according to claim 7, wherein the attachment flap further comprises at least one aperture therein corresponding to each of the at least one fixation tabs.

9. The expander according to claim 8, wherein the at least one aperture in the attachment flap is positioned so that the corresponding fixation tab may pass freely therethrough when the attachment flap is extended around the inferior edge and upward across at least a portion of the anterior side of the shell.

10. The expander according to claim 9, wherein the at least one aperture has a size and shape substantially similar to a size and shape of the corresponding fixation tab.

11. The expander according to claim 10, wherein the attachment flap further comprises a plurality of holes therethrough.

\* \* \* \* \*